(12) United States Patent
Yao et al.

(10) Patent No.: US 10,252,955 B2
(45) Date of Patent: Apr. 9, 2019

(54) SYSTEM FOR TWO STAGE UPGRADING OF LIGHT OLEFINS

(71) Applicant: PHILLIPS 66 COMPANY, Houston, TX (US)

(72) Inventors: Jianhua Yao, Bartlesville, OK (US); Hong Xie, Bartlesville, OK (US); Bruce B. Randolph, Bartlesville, OK (US); Steven E. Lusk, Ponca City, OK (US); Dhananjay B. Ghonasgi, Bartlesville, OK (US); Jonathan R. Marda, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 15/871,630

(22) Filed: Jan. 15, 2018

(65) Prior Publication Data

US 2018/0207626 A1    Jul. 26, 2018

Related U.S. Application Data

(60) Provisional application No. 62/448,744, filed on Jan. 20, 2017.

(51) Int. Cl.
| | | |
|---|---|---|
| *C07C 2/12* | (2006.01) | |
| *C07C 4/04* | (2006.01) | |
| *B01J 29/40* | (2006.01) | |
| *C07C 4/06* | (2006.01) | |
| *C07C 5/03* | (2006.01) | |
| *B01J 19/24* | (2006.01) | |

(52) U.S. Cl.
CPC ............... *C07C 2/12* (2013.01); *B01J 19/24* (2013.01); *B01J 29/40* (2013.01); *C07C 4/04* (2013.01); *C07C 4/06* (2013.01); *C07C 5/03* (2013.01); *B01J 2219/24* (2013.01); *C07C 2529/40* (2013.01)

(58) Field of Classification Search
CPC ... B01J 19/24; B01J 19/245; B01J 8/04; B01J 8/0278; C07C 2/12; C07C 2/42–2/52; C07C 4/04; C10G 50/00
See application file for complete search history.

(56) References Cited

U.S. PATENT DOCUMENTS

| | | | | |
|---|---|---|---|---|
| 4,433,185 A | * | 2/1984 | Tabak | C10G 50/00 585/312 |
| 2015/0175907 A1 | * | 6/2015 | Yao | C10G 57/02 585/256 |

* cited by examiner

*Primary Examiner* — Lessanework Seifu
(74) *Attorney, Agent, or Firm* — Phillips 66 Company

(57) ABSTRACT

The present disclosure relates generally processes and systems for converting a mixture of light hydrocarbons to liquid transportation fuels by first cracking the light hydrocarbons to an intermediate comprising olefins, which is converted by contacting with a catalyst comprising at least one zeolite in two separate conversion stages with an intervening recovery of liquid product. The first stage conversion favors oligomerization of larger olefins to form diesel range products that are collected prior to directing unconverted smaller olefins to be oligomerized in a second stage conversion conducted at a higher temperature and lower pressure.

6 Claims, 2 Drawing Sheets

SYSTEM FOR TWO STAGE UPGRADING OF LIGHT OLEFINS

CROSS-REFERENCE TO RELATED APPLICATIONS

This application is a non-provisional application which claims the benefit of and priority to U.S. Provisional Application Ser. No. 62/448,744 filed Jan. 20, 2017, titled "Systems for Two Stage Upgrading of Light Olefins," which is hereby incorporated by reference in its entirety.

STATEMENT REGARDING FEDERALLY SPONSORED RESEARCH OR DEVELOPMENT

None.

FIELD OF THE INVENTION

The present disclosure relates to processes and systems for converting light paraffins to liquid hydrocarbon transportation fuels.

BACKGROUND

Light paraffins produced alongside tight oil and natural gas are typically of lesser value than olefins or liquid fuels, and increased production of these light paraffins from U.S. shale formations has created a market surplus of natural gas liquids (NGL). After being extracted in the field, a largely de-methanized NGL stream largely comprising C2-C7 hydrocarbons (also called Y-grade), is typically transported by pipelines from the production site to a fractionation facility where the NGL stream is separated into discrete components, including ethane, propane, iso-butane, n-butane, and natural gasoline (C5+).

Several commercial upgrading options exist for these various components. Some techniques utilize an initial steam cracking step to upgrade these light paraffins, either individually or as a mixture. Other processes instead utilize catalytic processing in various forms. For example Oleflex™, STAR™, Catofin™, or FBD™ can be employed for propane and heavier paraffins, but require removal of ethane prior to upgrading of the heavier NGL components. This requirement is a disadvantage of these technologies, as is their high capital expense. As a result, commercial alternatives are not currently attractive. Accordingly, a need exists for a more efficient process that allows efficient upgrading of a mixture of C2-C7 light olefins (e.g., Y-grade or natural gas liquids) to liquid transportation fuels without first separating out one or more components.

BRIEF SUMMARY OF THE DISCLOSURE

The present inventive disclosure relates to methods and systems for converting a mixture of light hydrocarbons into products that can be used as a liquid transportation fuel, or a blend component thereof. The process relates to a two-stage conversion/upgrading that maintains or increases overall yield of products that can be utilized as a transportation fuel (relative to a conventional one-stage process), while improving yield of hydrocarbons in the diesel boiling-point range.

Certain embodiments comprise a method for converting a light hydrocarbon feedstock to produce liquid transportation fuels comprising: providing a light hydrocarbon feedstock comprising at least 80 wt % of hydrocarbon molecules that contain five or less carbon atoms; cracking and quenching the light hydrocarbon feedstock to produce a raw cracked olefins stream comprising ethylene, propylene, butenes, acetylene and dienes, hydrogen, methane and unconverted feedstock; contacting the raw cracked olefins stream with a first stage catalyst, where the catalyst, temperature and pressure in the first stage conversion reactor 25 are configured to produce a first stage effluent comprising at least 10 wt % of hydrocarbons that are characterized by a boiling point ranging from 193° C. to 360° C. at 1 atm; separating the first stage effluent in a first separator to produce a first condensed liquid hydrocarbons comprising at least five carbon atoms, and an unconverted light olefin stream comprising four or less carbon atoms; converting the uncondensed gas-phase hydrocarbons in a second stage reactor at a second temperature that is at least 20° C. higher than the first temperature, to produce a second stage effluent; and finally, separating the second stage effluent in a second separator to produce an unconverted light olefin stream comprising four or less carbon atoms, and a second condensed liquid hydrocarbons comprising at least five carbon atoms.

Optionally, the light hydrocarbon feedstock comprises at least 90 wt % of hydrocarbon molecules that contain five or less carbon atoms, or four or less carbon atoms. In certain embodiments, the light hydrocarbon feedstock comprises at least 97 wt % of hydrocarbon molecules that contain six or less carbon atoms.

In certain embodiments, the catalyst, temperature and pressure in the first-stage conversion reactor are configured to produce a first stage effluent comprising at least 15 wt % of hydrocarbons characterized by a boiling point ranging from 193° C. to 360° C. at 1 atm. In certain embodiments, the catalyst, temperature and pressure in the first-stage conversion reactor 25 are configured to produce a first stage effluent comprising at least 60 wt. % of hydrocarbon molecules characterized by a boiling point that ranges from 40° C. to 360° C.

In certain embodiments, the first stage conversion takes place at a temperature in the range between 180° C. and 300° C. and a pressure in the range between 300 psig and 800 psig. In certain embodiments, the first stage conversion occurs at a temperature in the range between 200° C. and 260° C. and a pressure in the range between 300 psig and 500 psig.

In certain embodiments, the second stage conversion takes place at a temperature in the range between 300° C. and 450° C. and a pressure in the range between about 14 psig and 300 psig. In certain embodiments, the second stage conversion occurs at a temperature in the range between 320° C. and 365° C. and a pressure in the range from 40 psig to 200 psig.

In certain embodiments, the temperature utilized for the second stage conversion is at least 25° C. higher than the temperature utilized for the first stage conversion. In certain embodiments, the pressure utilized for the second stage conversion is at least 100 psig less than the pressure utilized for the first stage conversion.

In certain embodiments, the catalyst in the first stage conversion reactor and the second stage conversion reactor comprises at least one zeolite, optionally impregnated with at least one metal, optionally the zeolite is ZSM-5 zeolite.

In certain embodiments, the catalyst and the conditions of temperature and pressure utilized in the first stage conversion are configured to produce more hydrocarbons (by wt.) characterized by a boiling point in a range from 193° C. to 360° C. (at 1 atm) than the second stage conversion.

In certain embodiments, the process further comprises mixing the first condensed liquid hydrocarbons and the second condensed liquid hydrocarbons to produce a final liquid product hydrocarbons comprising hydrocarbon molecules that are characterized by a boiling point that is within the boiling point range of gasoline (40° C. to 193° C.) or diesel (193° C. to 360° C.

In certain embodiments, the unconverted light olefin stream is separated into a light hydrocarbons recycle stream that is conveyed to mix with the light hydrocarbon stream upstream of the cracking unit and a hydrogen stream. In certain embodiments, at least 80 wt % of the light hydrocarbon stream is converted to final liquid product hydrocarbons.

Certain embodiments comprise a system for converting a light hydrocarbon feedstock to produce liquid transportation fuels, the system comprising: a supply of a light hydrocarbon feedstock comprising at least 80 wt % hydrocarbon molecules containing five or less carbon atoms; a cracking furnace configured to receive and thermally crack the light hydrocarbon feedstock at temperatures exceeding 450° C. to produce a cracked light hydrocarbon feedstock; a quench tower configured to receive and rapidly cool a cracked light hydrocarbon feedstock to produce a raw cracked olefins stream; a first stage conversion reactor configured to receive the raw cracked olefins stream facilitate contact between the raw cracked olefins stream and a catalyst bed comprising at least one zeolite, the first stage conversion reactor further configured to maintain a temperature in the range between 180° C. and 300° C. and a pressure in the range between 300 psig and 800 psig; a first separator configured to receive and partially condense an effluent from the first stage conversion reactor, the first separator additionally comprising an outlet for a first condensed liquid and an outlet for a first unconverted gas; a stage conversion reactor configured to receive the first unconverted gas from the first separator and facilitate contact between the first unconverted gas and a catalyst bed comprising at least one zeolite, the second stage conversion reactor further configured to maintain a temperature in the range between 300° C. and 450° C. and a pressure in the range between about 14 psig and 300 psig; a second separator configured to receive and partially condense an effluent from the second stage conversion reactor, the second separator additionally comprising an outlet for a second condensed liquid and an outlet for a second unconverted gas.

In certain embodiments of the system, the light hydrocarbon feedstock comprises at least 90 wt % of hydrocarbon molecules that contain five or less carbon atoms, optionally at least 90 wt % of hydrocarbon molecules that contain four or less carbon atoms, optionally at least 97 wt % of hydrocarbon molecules that contain six or less carbon atoms.

Certain embodiments of the system further comprise a conduit configured to convey the second unconverted gas to the cracking furnace. Certain embodiments of the system further comprise a separator configured to receive the second unconverted gas and perform pressure swing adsorption to separate a stream comprising hydrogen from the second unconverted gas, and a conduit configured to convey the remaining light hydrocarbons to mix with the supply of light hydrocarbon feedstock. Certain embodiments of the system further comprise a conduit configured to convey the hydrogen stream to a hydrotreater.

In certain embodiments of the system, the catalyst in the first stage conversion reactor and the second stage conversion reactor comprises at least one zeolite that is optionally impregnated with at least one metal and optionally ZSM-5.

BRIEF DESCRIPTION OF THE DRAWINGS

A more complete understanding of the present invention and benefits thereof may be acquired by referring to the follow description taken in conjunction with the accompanying drawings in which.

Figure 1:
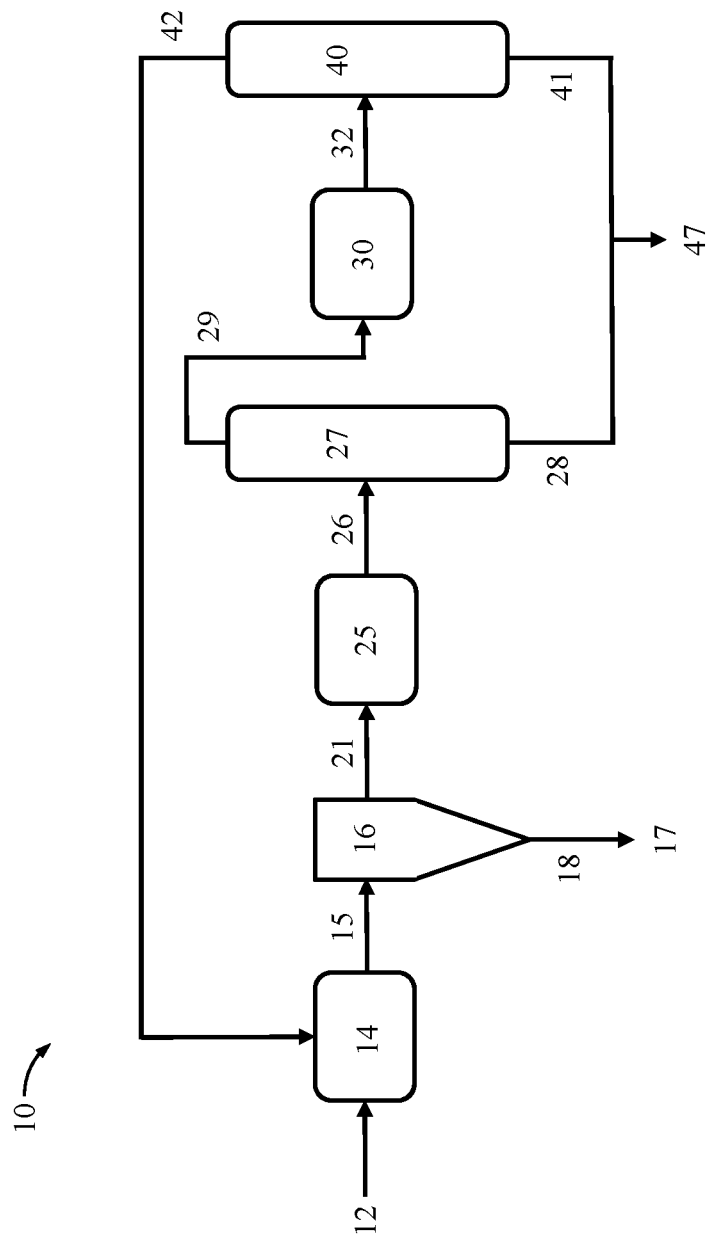
FIG. 1 is a diagram representing one embodiment of the inventive processes and systems.

The invention is susceptible to various modifications and alternative forms, specific embodiments thereof are shown by way of example in the drawings. The drawings may not be to scale. It should be understood that the drawings are not intended to limit the scope of the invention to the particular embodiment illustrated.

DETAILED DESCRIPTION

The present disclosure provides processes to convert a mixture of light hydrocarbons to liquid transportation fuels. The process and systems are applicable to the conversion of any mixture comprising predominantly light alkanes (i.e., C2-C7 alkanes). One example of such a mixture is a naturally-occurring mixture of hydrocarbons that is often referred to as "Y-grade" which is a sub-fraction of natural gas liquids that predominantly comprises ethane, propane, butanes and pentanes. The inventive processes and systems disclosed herein include a two-stage zeolite conversion process that increases the overall yield of liquid products that can be utilized as transportation fuel, and in particular, increases the yield of larger hydrocarbon products that can be used as a diesel transportation fuel, or a component thereof.

In its most basic form, the process comprises cracking and quenching a feed comprising light hydrocarbons to produce a raw cracked olefins stream comprising predominantly olefins, including ethylene, propylene, butenes, acetylene and dienes, but also hydrogen, methane, CO, $CO_2$ and unconverted feedstock.

The raw cracked olefin stream is then converted by contacting with a zeolite in two separate stages with an intervening collection of C5+ hydrocarbon products between stages. A first stage conversion reactor is optimized (temperature and pressure) to oligomerize olefins comprising at least three carbon atoms to produce larger hydrocarbon in the boiling point range of diesel. The first stage conversion produces an effluent comprising at least 70-75 wt. % of hydrocarbon molecules that are in the boiling-point range of gasoline, and at least 10 wt. % of hydrocarbon molecules that are in the boiling point range of #2 diesel. Preferably, the first stage conversion produces an effluent comprising at least 15 wt. % of hydrocarbon molecules that are in the boiling point range of #2 diesel.

Hydrocarbons comprising at least five carbon atoms are separated from the first stage effluent by condensation, then the remaining gas-phase hydrocarbons are converted/upgraded by contacting with a zeolite catalyst in a second stage reactor at a higher temperature that is optimized for the conversion of ethylene to larger hydrocarbons in the boiling point range of gasoline. and a second pressure that is lower than the first stage, to produce a product that comprises hydrocarbons suitable for use as liquid transportation fuels.

The present inventive process may utilize a conventional thermal cracking first step where thermal energy cracks the light hydrocarbon feedstream predominantly comprising a mixture of C2-C6 light hydrocarbons to form a raw cracked olefins stream comprising predominantly hydrogen, methane, acetylene, ethylene, ethane, propylene, propane, butadiene, butenes, butanes, and a small amount of C5+. Table I lists the main components of a thermally cracked Y-grade light hydrocarbon stream. Thermally cracking of light olefins is conventional, and thus will not be discussed further here.

TABLE I

Composition of a raw cracked olefins stream derived from cracking of Y-grade light hydrocarbon fraction of natural gas liquids.

| Component | |
|---|---|
| Hydrogen (wt. %) | 22.4 |
| C1-C4 Alkanes (wt. %) | 37.7 |
| Ethylene (wt. %) | 30.2 |
| Propylene (wt. %) | 6.1 |
| Butenes (wt. %) | 1.1 |

The next step in the present inventive process comprises converting the light olefins in the raw cracked olefins stream to transportation fuels via a two stage processes over catalyst beds comprising a zeolite. In certain embodiments, the zeolite catalyst is ZSM-5, although many zeolites are well-understood in the art that may be suitable for use (either alone or in combination) with the inventive processes and systems described herein. A representative example (provided below) demonstrates the non-obvious advantage of conducting this conversion in two separate stages with each stage configured to achieve conversion of different components of the light hydrocarbon feedstock. Different temperatures and pressures are utilized in each stage, with an intermediate separation to recover C5+ products produced in the first stage.

One embodiment of the inventive processes and systems is illustrated in FIG. 1. A mixture of light hydrocarbons is converted to liquid transportation fuel in a system 10. A light hydrocarbons stream 12 comprises predominantly alkanes comprising 2-5 carbon atoms. Light hydrocarbons stream 12 is fed directly into a cracking furnace 14. The thermal cracking of hydrocarbons is typically a non-catalytic process relying on sufficient pressure and temperature in a furnace (such as cracking furnace 14). However, many catalytic processes for cracking light hydrocarbons are well-characterized, and are also acceptable for the present invention. Referring again to FIG. 1, cracking furnace 14 produces a raw cracked gas stream (not depicted) comprising predominantly hydrogen, methane, acetylene, ethylene, ethane, propylene, propane, butadiene, butenes, butanes and a small amount of C5+ along with trace amounts of other hydrocarbons. All of these products are suitable for subsequent two-stage conversion (described in greater detail below).

Again referring to FIG. 1, the raw cracked gas stream is conveyed to a quench tower 16 via a furnace conduit 15 to rapidly cool the raw cracked gas stream and prevent additional cracking reactions. The raw cracked gas stream is condensed in the quench tower 16 to produce liquid product termed pyrolysis gasoline 17 that comprises molecules containing five or more carbon atoms that exits the quench tower 16 via quench tower outlet 18. The pyrolysis gasoline 17 may be used as transportation fuel blend stock or may be further processed in another refinery process. A portion of the raw cracked gas stream that is not condensed in the quench tower 16 forms a raw light olefin stream (not depicted) comprising light olefins and alkanes containing four or less carbon atoms.

The raw light olefin stream exits the quench tower 16 via quench tower conduit 21, which conveys the raw light olefin stream into a first-stage conversion reactor 25. The first-stage conversion reactor 25 includes a catalyst bed comprising at least one zeolite catalyst (not depicted) that converts the raw light olefin stream into products that include hydrocarbons comprising at least five carbon atoms. In certain embodiments, this zeolite is ZSM-5. In the present disclosure, the term "conversion" is defined as any of the chemical reactions that occur during zeolite upgrading of hydrocarbons to liquid transportation fuels. Examples of such reactions include, but are not limited to: oligomerization, hydrogenation and cracking.

The first stage conversion reactor 25 is maintained at conditions of temperature and pressure that favor the oligomerization of olefins comprising at least three carbons atoms to produce a first stage product (not depicted) comprising hydrocarbons that, in turn, comprise at least five carbon atoms, more preferably, at least 7 carbons, and even more preferably, hydrocarbon products characterized by a boiling point ranging from 193° C. to 360° C., which is within the boiling point range of #2 diesel fuel.

Optimally, the catalyst, temperature and pressure in the first-stage conversion reactor 25 are configured to facilitate the formation of hydrocarbons characterized by a boiling point ranging from 193° C. to 360° C. at 1 atm. In certain embodiments, at least 10 wt % (optionally, at least 15 wt %) of the raw light olefin stream that enters the first-stage conversion reactor 25 is converted to product hydrocarbons having a boiling point (at 1 atm) ranging from 193° C. to 360° C.

The first stage product exits the first-stage conversion reactor 25 and is conveyed via first stage product conduit 26 to a first separator 27 that is maintained at a temperature that allows the condensation of hydrocarbons comprising at least five carbon atoms. A first stage Condensed liquid hydrocarbons (not depicted) exits the first separator by gravity flow via first separator conduit 28.

Meanwhile, an unconverted light olefin stream (not depicted) comprising hydrocarbons characterized by four or less carbon atoms remains in vapor-phase and exits the first separator 27 via unconverted light olefin conduit 29. The unconverted light olefin stream predominantly comprises unconverted ethylene and ethane, but also may include some residual olefins and alkanes comprising three or four carbon atoms that were not converted to larger hydrocarbons in the first stage conversion reactor The unconverted light olefin stream is conveyed via unconverted light olefin conduit 29 to a second stage conversion reactor 30 containing at least one zeolite catalyst. The second-stage conversion reactor 30 includes a catalyst bed comprising at least one zeolite catalyst (not depicted) suitable to convert the unconverted light olefin stream into larger hydrocarbon products comprising at least five carbon atoms.

Conditions of temperature and pressure are maintained in the second-stage conversion reactor 30 to favor the oligomerization of ethylene to form larger hydrocarbon products that preferably comprise at least five carbon atoms, more preferably, at least 7 carbons. The operating conditions for the second-stage conversion reactor 30 generally include a pressure in a range of between 14 psig and 800 psig, a temperature in a range of between 260° C. and 420° C., and a feedstock feed rate (measured as a gas hourly space velocity) in a range of between 1000 and 5000 inverse hours. While higher overall productivity is desirable, ideally at least 85% of the ethylene is converted.

In certain embodiments, the first stage conversion takes place at a temperature in the range between 180° C. and 300° C. and a pressure in the range between 300 psig and 800 psig, while the subsequent second stage conversion typically takes place at a temperature in the range between 300° C. and 450° C. and a pressure in the range from about 14 psig to 300 psig. In certain embodiments, the first stage conversion takes place at a temperature in the range between 200° C. and 260° C. and a pressure in the range between 300 psig and 500 psig, while the subsequent second stage conversion takes place at a temperature in the range between 320° C. and 365° C. and a pressure in the range from 40 psig to 200 psig.

In certain embodiments, the temperature utilized for the second stage conversion is at least 25° C. higher (optionally at least 40° C. higher, optionally at least 50° C. higher, optionally at least 60° C. higher) than the temperature utilized for the first stage conversion. In certain embodiments, the pressure utilized for the second stage conversion is at least 100 psig less (optionally at least 200 psig less) than the pressure utilized for the first stage conversion.

Again referring to FIG. 1, a second stage effluent from the second stage catalytic oligomerization reactor 30 is conveyed via an second stage outlet conduit 32 to a second separator 40 that separates the products into two fractions. A second condensed liquid hydrocarbons comprising hydrocarbon molecules containing at least five carbon atoms exits the bottom of the second separator 40 via second separator C5+ product conduit 41. The second stage condensed liquid hydrocarbons is combined with the first stage condensed liquid hydrocarbons from the first product separator 27 to produce a final liquid hydrocarbon product 47 that may be blended into conventional liquid transportation fuels or additionally processed (i.e., hydrotreating) prior to use as a transportation fuel. In certain embodiments, hydrocarbons in the diesel boiling point range may be separated from the final liquid hydrocarbon product, then further hydrotreated to reduce olefin and aromatic contents via hydrotreating or hydrogenation using a conventional hydrotreating catalyst (such as NiMo, CoMo, etc.) or a precious metal catalyst (such as Pt/Al2O3, Pd/Al2O3, or Pd/C, etc).

Any remaining unconverted light gases (not depicted) leave the second separator 40 via unconverted gas conduit 42, which is recycled to the cracking furnace 14 to be combusted and provide at least a portion of the heat required for thermal cracking the light hydrocarbons stream 12.

Figure 2:
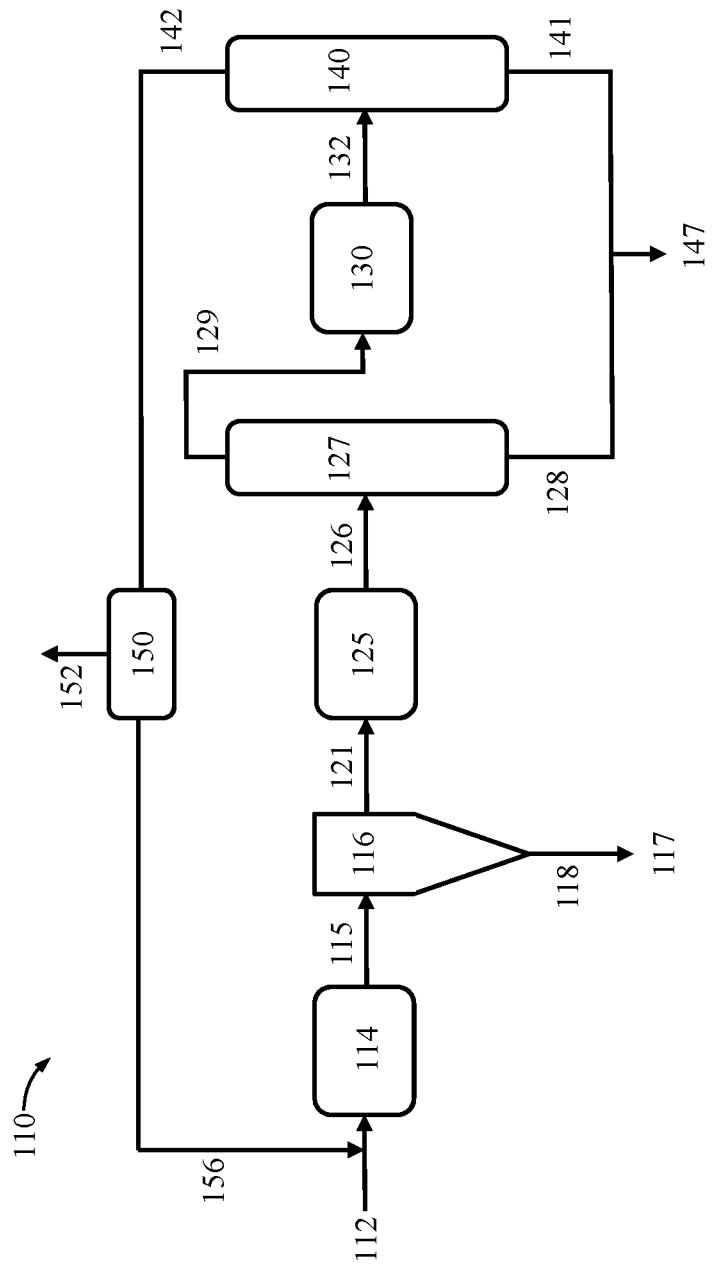
FIG. 2 is a diagram representing one embodiment of the inventive processes and systems.

FIG. 2 depicts a second embodiment, where the unconverted light gases are subjected to separation into a hydrogen component and a light gas component that predominantly comprises methane and ethane. The light gas component is mixed with the incoming light hydrocarbon stream upstream from the cracking furnace.

Referring to FIG. 2, a mixture of light hydrocarbons is converted to liquid transportation fuel in a system 110. A light hydrocarbon stream 112 comprises predominantly alkanes comprising from two to six carbon atoms. Light hydrocarbon stream 112 is fed directly into a cracking furnace 114 to produce a thermally-cracked raw cracked gas stream (not depicted) comprising predominantly hydrogen, methane, acetylene, ethylene, ethane, propylene, propane, butadiene, butenes, butanes and a small amount of C5+ along with trace amounts of other hydrocarbons. All of these products are suitable for subsequent two-stage conversion over at least one zeolite catalyst (described in greater detail below).

The raw cracked gas stream is conveyed to a quench tower 116 via a furnace conduit 115 to rapidly cool the raw cracked gas stream and prevent additional cracking reactions. The raw cracked gas stream is condensed in the quench tower 116 to produce liquid product termed pyrolysis gasoline 117 that comprises molecules containing five or more carbon atoms that exits the quench tower 116 via quench tower outlet 118. The pyrolysis gasoline 117 may be used as transportation fuel blend stock or may be further converted in another refinery process. A portion of the raw cracked gas stream that is not condensed in the quench tower 116 forms a raw light olefin stream (not depicted) comprising light olefins and alkanes containing four or less carbon atoms.

The raw light olefin stream exits the quench tower 116 via quench tower conduit 121, which conveys the raw light olefin stream into a first-stage conversion reactor 125. The first-stage conversion reactor 125 includes a catalyst bed comprising at least one zeolite catalyst (not depicted) that converts the raw light olefin stream into products that include hydrocarbons comprising at least five carbon atoms. In certain embodiments, this zeolite catalyst bed comprises ZSM-5. In the present disclosure, the term "conversion" is defined as any of the chemical reactions that occur during zeolite upgrading of hydrocarbons to liquid transportation fuels. Examples of such reactions include, but are not limited to: oligomerization, hydrogenation and cracking.

The first stage conversion reactor 125 is maintained at conditions of temperature and pressure that favor the oligomerization of olefins comprising at least three carbons atoms to produce a first stage condensed liquid hydrocarbons (not depicted) comprising hydrocarbons that, in turn, comprise at least five carbon atoms, more preferably, at least seven carbons, and even more preferably, hydrocarbon products characterized by a boiling point in the range from 193° C. to 360° C. at 1 atm, which is within the boiling point range of #2 diesel fuel.

Optimally, the conditions of temperature and pressure utilized in the first-stage conversion reactor 125 facilitate the formation of hydrocarbons characterized by a boiling point in the range from 193° C. to 360° C. at 1 atm. In certain embodiments, at least 10 wt % (optionally, at least 15 wt %) of the raw light olefin stream that enters the first-stage conversion reactor 125 is converted to product hydrocarbons having a boiling point in the range from 193° C. to 360° C. at 1 atm.

The first stage product exits the first-stage conversion reactor 125 and is conveyed via first stage product conduit 126 to a first separator 127 that is maintained at a temperature that allows the condensation of hydrocarbons comprising at least five carbon atoms. A first stage condensed liquid hydrocarbons (not depicted) exits the first separator by gravity flow via first separator conduit 128.

Meanwhile, an unconverted light olefin stream (not depicted) comprising hydrocarbons characterized by four or less carbon atoms remains in vapor-phase and exits the first separator 127 via unconverted light olefin conduit 129. The unconverted light olefin stream predominantly comprises unconverted ethylene and ethane, but also may include some residual olefins and alkanes comprising three or four carbon atoms that were not converted to larger hydrocarbons in the first stage conversion reactor.

The unconverted light olefin stream is conveyed via unconverted light olefin conduit 129 to a second stage conversion reactor 130 containing at least one zeolite catalyst. The second-stage conversion reactor 130 includes a catalyst bed comprising at least one zeolite catalyst (not depicted) suitable to convert the unconverted light olefin stream into larger hydrocarbon products comprising at least five carbon atoms.

A second stage effluent from the second stage conversion reactor 130 is conveyed via a second stage outlet conduit 132 to a second separator 140 that separates the products into two fractions. A second condensed liquid hydrocarbons comprising hydrocarbon molecules containing at least five carbon atoms exits the bottom of the second separator 140 via second separator C5+ product conduit 141. The second condensed liquid hydrocarbons is combined with the first condensed liquid hydrocarbons from the first product separator 127 to produce a final liquid hydrocarbon product 147 that may be blended into conventional liquid transportation fuels or additionally processed prior to use as a transportation fuel. In certain embodiments, hydrocarbons characterized by a boiling point in the range from 193° C. to 360° C. (i.e., diesel-range hydrocarbons) may be separated from the final liquid hydrocarbon product, then further hydrotreated to reduce olefin and aromatic contents via hydrotreating or hydrogenation using a conventional hydrotreating catalyst (such as NiMo, CoMo, etc.) or a precious metal catalyst (such as Pt/Al2O3, Pd/Al2O3, or Pd/C, etc).

Again referring to FIG. 2, any remaining unconverted light gases (not depicted) leave the second separator 140 via unconverted gas conduit 142, which is introduced into a third separation unit 150 that utilizes a conventional separation technology (such as, but not limited to, pressure swing adsorption technology, membrane separation technology, etc.) to separate hydrogen from light hydrocarbons to produce a hydrogen stream 152 (that may optionally be utilized for hydrotreating the final liquid hydrocarbon product) and light hydrocarbons recycle stream (not depicted) that is then conveyed via light hydrocarbons recycle conduit 156 to mix with the light hydrocarbons stream 112 upstream from the cracking furnace 114.

The dual-stage light olefin conversion/upgrading process and systems disclosed herein provide a clear advantage when compared to a conventional single-stage light olefin conversion. The present process utilizes milder temperature conditions and higher pressures in the first stage to optimize the conversion of larger olefins (e.g., propene and butenes) to hydrocarbon products that have a boiling point in a range from 193° C. to 360° C. (in the range of #2 diesel). These diesel-range hydrocarbons products are then condensed and separated from unconverted light hydrocarbons (predominantly ethylene) following the first stage to prevent cracking of the diesel-range product hydrocarbons if they were to be exposed to the higher temperatures maintained in the second stage conversion reactor.

By design, ethylene present in the raw light olefin stream remains largely unconverted in the first stage conversion reactor. Once C5+ hydrocarbons are separated and recovered in the first separator, the remaining unconverted light olefin stream (comprising mostly ethylene, ethane and methane) is converted in a second stage at a higher temperature (and lower pressure) that provides the additional energy needed to efficiently oligomerized the ethylene present in the unconverted light olefin stream. The effluent from this second-stage conversion reactor is then send to a second product separator to condense C5+ hydrocarbons, which are then combined with the condensed product from the first-stage conversion reactor.

Results provided in the example below indicate that the two-stage processes and systems disclosed herein not only increase the overall yield of hydrocarbons products comprising five or more carbons (in the boiling point range of either gasoline or diesel) but also significantly increase the yield of product hydrocarbon molecules characterized by a boiling point above 193° C. (i.e., in the boiling point range of diesel). The example below shows that the present two stage zeolite conversion process produced 17.9 wt. % of hydrocarbons characterized by a boiling point in the diesel boil point range (from 193° C. to 360° C.) while a conventional single step zeolite conversion formed only 5.8 wt. % of diesel-range products. This implies that the additional diesel-range product is formed in the first stage of the inventive process, which is optimized for the oligomerization of C3-C4 olefins to form larger products, but is not conducive to the oligomerization of ethylene.

The second stage conversion reactor is maintained at a higher temperature and lower pressure than the first stage reactor, which favors conversion of the remaining ethylene in the unconverted light olefin stream to form predominantly hydrocarbons in the boiling point range of gasoline. An additional advantage of the present inventive process is that separating out hydrocarbons comprising at least five carbon atoms (in the first separator) prior to conducting the second stage conversion increases the yield of larger diesel-range products by preventing the cracking of these larger hydrocarbons at the higher temperatures maintained in the second stage conversion reactor.

The following example is representative of one embodiment of the inventive processes and systems disclosed herein, and the scope of the invention is not intended to be limited to the embodiment specifically disclosed. Rather, the scope is intended to be as broad as is supported by the complete disclosure and the appending claims.

EXAMPLE

To demonstrate the effectiveness of the dual stage conversion process disclosed herein, we compared a conventional one-stage zeolite conversion of light olefins to one embodiment of the inventive two stage process disclosed herein. A simulated cracked light olefin feedstock was utilized that comprised 23 mole % hydrogen, 23 mole % methane, 14 mole % ethane, 31 mole % ethylene, 6.5 mole % propylene, and 2.5 mole % 1-butene. This feedstock was designed to replicate a typical raw cracked olefin stream derived from the thermal cracking of a light hydrocarbon feedstock. The feedstock was introduced to a first stage reactor containing a ZSM-5 zeolite catalyst. The reactor was maintained at a temperature of 250° C. and pressure of 360 psig. The effluent from this zeolite conversion reactor was then condensed to recover C5+ liquid hydrocarbons.

Hydrocarbons that remained unconverted by the relatively mild conditions of the first stage reactor were next introduced to a second reactor containing ZSM-5 zeolite and maintained at 320° C. and 50 psig to convert remaining light olefins. Analysis of the combined liquid products condensed from the reactor was combined with the liquid product from the first conversion/upgrading reactor and the overall product distribution is reported in Table 1. The dual stage conversion process was observed to clearly improve the overall liquid yield as well as the yield of product hydrocarbons having a boiling point in the range of diesel. The quantity of C5+ condensable hydrocarbons collected after the 1st stage was 28.8 g (includes both gasoline-range and diesel-range hydrocarbons), while the C5+ condensable hydrocarbons collected after the second stage was about 95.4 g. Therefore, the first stage reaction produced about 23 wt. % (28.8/(28.8+95.4)*100=23%) of the overall C5+ condensable hydrocarbons that were collected.

TABLE 1

Comparison of converting mixed light olefins to liquid hydrocarbon fuels on ZSM-5 catalyst using single stage process vs. dual stage process

| Conversion Process | Single Stage | Two Stage | |
|---|---|---|---|
| | | Stage 1 | Stage 2 |
| Time on stream (hrs) | | | |
| Temp (° C.) | 320 | 250 | 320 |
| Pressure (psig) | 50 | 360 | 50 |
| LHSV (hr-1) | 1 | 1 | 1 |
| Product selectivity (wt %) | | | |
| C1-C3 | 6.8 | | 8.4 |
| C4 | 18.7 | | 7.2 |
| C5-380 F (Gasoline) | 68.7 | | 66.4 |
| 380 F-680 F (Diesel) | 5.8 | | 17.9 |
| Liquid Selectivity (wt %) | | | |
| Gasoline + Diesel | 75.4 | | 84.3 |
| Light Olefin Conversion (%) | 98.7 | | 96.0 |

In closing, it should be noted that the discussion of any reference is not an admission that it is prior art to the present disclosure, in particular, any reference that may have a publication date after the priority date of this application. At the same time, each and every claim below is hereby incorporated into this detailed description or specification as a additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

We claim:

1. A system for converting a light hydrocarbon feedstock to produce liquid transportation fuels, the system comprising:
    a) a supply of a light hydrocarbon feedstock comprising at least 80 wt % hydrocarbon molecules containing five or less carbon atoms;
    b) a cracking furnace configured to receive and thermally crack the light hydrocarbon feedstock at temperatures exceeding 450° C. to produce a cracked light hydrocarbon feedstock;
    c) a quench tower configured to receive and rapidly cool a cracked light hydrocarbon feedstock to produce a raw cracked olefins stream;
    d) a first stage conversion reactor configured to receive the raw cracked olefins stream and facilitate contact between the raw cracked olefins stream and a catalyst bed comprising at least one zeolite, the first stage conversion reactor further configured to maintain a temperature in the range between 180° C. and 300° C. and a pressure in the range between 300 psig and 500 psig;
    e) a first separator configured to receive and partially condense an effluent from the first stage conversion reactor, the first separator additionally comprising an outlet for a first condensed liquid and an outlet for a first unconverted gas;
    f) a second stage conversion reactor configured to receive the first unconverted gas from the first separator and facilitate contact between the first unconverted gas and a catalyst bed comprising at least one zeolite, the second stage conversion reactor further configured to maintain a temperature in the range between 300° C. and 450° C. and a pressure in the range between about 14 psig and 300 psig;
    g) a second separator configured to receive and partially condense an effluent from the second stage conversion reactor, the second separator additionally comprising an outlet for a second condensed liquid and an outlet for a second unconverted gas.

2. The system of claim 1, further comprising a conduit configured to convey the second unconverted gas of g) to the cracking furnace.

3. The system of claim 1, further comprising a separator configured to receive the second unconverted gas and perform pressure swing adsorption to separate a hydrogen stream comprising hydrogen from the second unconverted gas, and a conduit configured to convey the remaining light hydrocarbons to mix with the supply of light hydrocarbon feedstock.

4. The system of claim 3, further comprising a conduit configured to convey the hydrogen stream to a hydrotreater.

5. The system of claim 1, wherein the catalyst in the first stage conversion reactor and the second stage conversion reactor comprises at least one zeolite.

6. The system of claim 1, wherein the catalyst in the first stage conversion reactor and the second stage conversion reactor comprises ZSM-5 zeolite.

* * * * *